United States Patent [19]
Nishiyama et al.

[11] Patent Number: 5,929,281
[45] Date of Patent: Jul. 27, 1999

[54] PROCESS FOR PRODUCING HETEROCYCLIC AROMATIC AMINE OR ARYLAMINE

[75] Inventors: Masakazu Nishiyama, Yokkaichi; Yasuyuki Koie, Inabe-gun, both of Japan

[73] Assignee: Tosoh Corporation, Japan

[21] Appl. No.: 08/834,231

[22] Filed: Apr. 15, 1997

[30] Foreign Application Priority Data

Apr. 19, 1996 [JP] Japan ................................ 8-098388
Jul. 15, 1996 [JP] Japan ................................ 8-184469
Sep. 12, 1996 [JP] Japan ................................ 8-241724

[51] Int. Cl.$^6$ ................... C07C 209/00; C07C 209/10
[52] U.S. Cl. ................... 564/386; 564/148; 564/374; 564/376; 564/144; 564/391; 564/395; 564/405; 564/407; 544/358; 544/392; 544/106; 544/197; 544/359; 544/373; 546/15; 546/23; 546/24

[58] Field of Search .................... 544/359, 358, 544/392, 106, 197, 373; 564/358, 374, 376, 391, 395, 405, 407; 546/15, 23, 24

[56] References Cited

U.S. PATENT DOCUMENTS 5,576,460  11/1996  Buchwald et al. ..................... 564/386

OTHER PUBLICATIONS

Grigg. et al., J. Chem. Soc. Chem. Commun., vol. 18, pp. 1903–1904, 1995.

Wolfe et al., J. Org. Chem. vol. 61, pp. 1133–1135, 1996.

Tafesh et al., Tetrahedron Letters, vol. 36, No. 51, 9305–8, 1995.

Tolman A. Chadwick, Chem. Rev., vol. 77, No. 3, pp. 313–348, 1977.

J. Am. Chem. Doc., vol. 116, No. 17, 1994 p. 7901–7902.

Angew. Chem. Int. Ed. Engl. 1995, 34, No. 12 p. 1348–1350.

*Primary Examiner*—José G. Dees
*Assistant Examiner*—Sabiha N. Qazi
*Attorney, Agent, or Firm*—Nixon & Vanderhye P.C.

[57] ABSTRACT

A heterocyclic aromatic halide or an aryl halide is reacted with an amine compound in the presence of a base to give a heterocyclic aromatic amine or an arylamine, respectively. In this reaction, a catalyst comprising a palladium compound and a tertiary phosphine is used for the preparation of a heterocyclic aromatic amine, and a catalyst comprising a palladium compound and a trialkylphosphine is used for the preparation of an arylamine.

2 Claims, No Drawings

PROCESS FOR PRODUCING HETEROCYCLIC AROMATIC AMINE OR ARYLAMINE

BACKGROUND OF THE INVENTION (1) Field of the Invention

This invention relates to a process for preparing a heterocyclic aromatic amine or an arylamine, which is an important intermediate in pharmaceutical and pesticide applications.

(2) Description of the Related Art

Processes are known wherein a heterocyclic aromatic halide or an aryl halide is allowed to react with an amine to give a heterocyclic aromatic amine or an arylamine, respectively, by using a copper catalyst (see, for example, Dai-yuki Kagaku [Organic Chemistry] vol. 16, 52 (1959) published by Asakura Shoten; and Yuki Kagaku Koza [Lectures on Organic Chemistry] 3, 66 (1983) published by Maruzen). In the processes using a copper catalyst, the yield of an arylamine or a heterocyclic aromatic amine is low because a salient amount of the catalyst must be used and a high reaction temperature is required. Further, the arylamine or the heterocyclic aromatic amine is difficult to purify from the reaction system because the reaction products are inevitably colored to a large extent.

Recently Stephen L. Buchwald et al have reported a process for synthesizing an arylamine from an aryl halide and an amine compound [Angew. Chem. Int. Ed. Engl., 34, No. 12, 1348 (1995]. In this process, an aryl bromide is allowed to react with an amine in the presence of sodium tert-butoxide as a base by using a catalyst comprising a palladium compound having tri-o-tolyl phosphine as a ligand, i.e., bis(dibenzylidene-acetone)-bis(tri-o-tolylphosphine)palladium or dichloro-bis(tri-o-tolylphosphine)palladium. An analogous process has been reported by John F. Hartwig et al in Tetrahedron Letters, vol. 36, No. 21, 3609 (1995).

Further a process has been reported wherein an arylamine is synthesized from an aryl iodide by using a catalyst comprising a palladium compound having tri-o-tolylphosphine as a ligand in J. Org. Chem., 61, 1133 (1996).

In the processes using a palladium compound having tri-o-tolylphosphine as a ligand, especially when an amine compound having a hydrogen atom on the carbon α to the nitrogen atom is reacted with an aryl halide, a salient amount of bisaryl derivatives are produced each from two molecules of the aryl halide and a salient amount of arene derivatives are produced by dehalogenation, with the result of reduction in the yield of an intended arylamine. Further the amount of the palladium compounds described in the above reports used is large, i.e., 1 to 5% by mole per mole of the aryl halide, and thus the processes are costly.

SUMMARY OF THE INVENTION

By extensive researches to solve the problems existing in the prior art, the inventors have found that a catalyst comprising a tertiary phosphine and a palladium compound exhibits a high activity for the synthesis of a heterocyclic aromatic amine from a heterocyclic aromatic halide and thus the heterocyclic aromatic amine can be synthesized at a high selectivity by using this catalyst, and further that a catalyst comprising a trialkylphosphine and a palladium compound exhibits a high activity for the synthesis of an arylamine from an aryl halide such as aryl bromide, aryl iodide, aryl chloride or aryl fluoride and thus the arylamine can also be synthesized at a high selectivity with the minimized production of bis-aryl derivatives and dehalogenated arene derivatives, by using this catalyst.

In one aspect of the present invention, there is provided a process for producing a heterocyclic aromatic amine wherein a heterocyclic aromatic halide is reacted with an amine compound in the presence of a base, characterized in that the reaction of the heterocyclic aromatic halide with the amine compound is effected by using a catalyst comprising a tertiary phosphine and a palladium compound.

In another aspect of the present invention, there is provided a process for producing an arylamine wherein an aryl halide is reacted with an amine compound in the presence of a base, characterized in that the reaction of the aryl halide with the amine compound is effected by using a catalyst comprising a trialkylphosphine and a palladium compound.

DESCRIPTION OF THE PREFERRED EMBODIMENTS

The heterocyclic aromatic halide used as a starting material in the process of the invention is not particularly limited provided that it has at least one halogen atom bound to a heterocyclic aromatic compound. The heterocyclic aromatic halide may have one or more substituents such as an alkyl group, alkoxy group, a phenoxy group, a trifluoro-methyl group and an acyl group. By the term "heterocyclic aromatic compound" used in this specification we mean a compound having an aromatic ring with at least one hetero atom selected from nitrogen, sulfur and oxygen.

As specific examples of the heterocyclic aromatic halide used in the process of the invention, there can be mentioned oxygen-containing heterocyclic aromatic halides such as 3-bromofuran and bromobenzofuran; sulfur-containing heterocyclic aromatic halides such as 3-bromothiophene, 2-bromothiophene, 2,3-dibromothiophene, 2,5-dibromothiophene, 2-iodothiophene, 2,5-dichlorothiophene, 2,5-diiodothiophene, 2-chlorothiophene, 3,4-dibromothiophene, 3-chlorothiophene, 5-bromo-2-thiophenecarboxylic aldehyde and 2-bromo-5-chlorothiophene; monocyclic nitrogen-containing heterocyclic aromatic halides such as 2,3,4-tribromoimidazole, 4,5-dichloroimidazole, 5-chloro-1-ethyl-2-methylimidazole, 5-chloro-1-methylimidazole, 5-chloro-2-(trichloromethyl)benzimidazole, 4-bromo-3,5-dimethylpyrazole, 4-bromo-3-methylpyrazole, 4-bromopyrazole, 2-bromopyridine, 3-bromopyridine, 4-bromopyridine, 2,6-dibromopyridine, 2,5-dibromopyridine, 3,5-dibromopyridine, 2,3-dichloropyridine, 2,5-dichloropyridine, 2,6-dichloropyridine, 2-chloro-5-(trifluoromethyl)pyridine, 2-chloro-6-methoxypyridine, 2-chloronicotinamide, 2-chloropyridine, 3,5-dichloropyridine, 3-chloropyridine, 5-chloro-2-pyridinol, 5-chloro-3-pyridinol, 6-chloro-2-picoline, 2,6-difluoropyridine, 2-fluoropyridine, 3-fluoropyridine, 6-iodo-2-picolin-5-ol, 2,4-dichloropyrimidine, 5-bromopyrimidine, 2,6-dichloropyrazine, 3-chloro-2,5-dimethylpyrazine, chloropyrazine, 3,6-dichloropyridazine and 3-chloro-6-methoxypyridazine; and polycyclic nitrogen-containing heterocyclic aromatic halides such as 5-bromoindole, 4-chloroindole, 5-chloro-2-methylindole, 5-chloroindole, 5-fluoroindole, 6-chloroindole, 6,9-dichloro-2-methoxyacridine, 4-bromoisoquinoline, 3-bromoquinoline, 8-bromoquinoline, 4,7-dichloroquinoline, 4-bromo-2,8-bis(trifluoromethyl)quinoline, 4-chloro-7-(trifluoromethyl)quinoline, 4-chloro-8-(trifluoromethyl)quinoline, 4-chloroquinaldine, 4-chloroquinoline, 5,7-dibromo-2-methyl-8-quinolizinol, 5,7-dichloro-2-methyl-8-quinolizinol, 5,7-diiodo-8-hydroxyquinoline, 6-chloroquinoline and 7-chloroquinaldine.

The aryl halide used as a starting material in the process of the present invention is not particularly limited, and includes an aryl chloride, an aryl bromide, an aryl iodide and an aryl fluoride, and those which have one or more substituents bound to the aromatic ring, such as an alkyl group, an alkoxy group, a phenoxy group, a trifluoromethyl group or an acyl group. By the term "aryl" used in this specification we mean not only non-fused aromatic ring hydrocarbons but also fused aromatic ring hydrocarbon groups.

As specific examples of the aryl halide used in the process of the invention, there can be mentioned aryl bromides such as bromobenzene, o-bromoanisole, m-bromoanisole, p-bromoanisole, o-bromotoluene, m-bromotoluene, p-bromotoluene, o-bromophenol, m-bromophenol, p-bromophenol, 2-bromobenzotrifluoride, 3-bromobenzotrifluoride, 4-bromobenzotrifluoride, 1-bromo-2,4-dimethoxybenzene, 1-bromo-2,5-dimethoxybenzene, 2-bromophenethyl alcohol, 3-bromophenethyl alcohol, 4-bromophenethyl alcohol, 5-bromo-1,2,4-trimethylbenzene, 2-bromo-m-xylene, 2-bromo-p-xylene, 3-bromo-o-xylene, 4-bromo-o-xylene, 4-bromo-m-xylene, 5-bromo-m-xylene, 1-bromo-3-(trifluoromethoxy)benzene, 1-bromo-4-(trifluoromethoxy)benzene, 2-bromobiphenyl, 3-bromobiphenyl, 4-bromobiphenyl, 4-bromo-1,2-(methylenedioxy)benzene, 1-bromonaphthalene, 2-bromonaphthalene, 1-bromo-2-methylnaphthalene and 1-bromo-4-methylnaphthalene; aryl chlorides such as chlorobenzene, o-chloroanisole, m-chloroanisole, p-chloroanisole, o-chlorotoluene, m-chlorotoluene, p-chlorotoluene, o-chlorophenol, m-chlorophenol, p-chlorophenol, 2-chlorobenzotrifluoride, 3-chlorobenzotrifluoride, 4-chlorobenzotrifluoride, 1-chloro-2,4-dimethoxybenzene, 1-chloro-2,5-dimethoxybenzene, 2-chlorophenethyl alcohol, 3-chlorophenethyl alcohol, 4-chlorophenethyl alcohol, 5-chloro-1,2,4-trimethylbenzene, 2-chloro-m-xylene, 2-chloro-p-xylene, 3-chloro-o-xylene, 4-chloro-o-xylene, 4-chloro-m-xylene, 5-chloro-m-xylene, 1-chloro-3-(trifluoromethoxy)benzene, 1-chloro-4-(trifluoromethoxy)benzene, 2-chlorobiphenyl, 3-chlorobiphenyl, 4-chlorobiphenyl, 1-chloronaphthalene, 2-chloronaphthalene, 1-chloro-2-methylnaphthalene and 1-chloro-4-methylnaphthalene; aryl iodides such as iodobenzene, o-iodoanisole, m-iodoanisole, p-iodoanisole, o-iodotoluene, m-iodotoluene, p-iodotoluene, o-iodophenol, m-iodophenol, p-iodophenol, 2-iodobenzotrifluoride, 3-iodobenzotrifluoride, 4-iodobenzotrifluoride, 1-iodo-2,4-dimethoxybenzene, 1-iodo-2,5-dimethoxybenzene, 2-iodophenethyl alcohol, 3-iodophenethyl alcohol, 4-iodophenethyl alcohol, 5-iodo-1,2,4-trimethylbenzene, 2-iodo-m-xylene, 2-iodo-p-xylene, 3-iodo-o-xylene, 4-iodo-o-xylene, 4-iodo-m-xylene, 5-iodo-m-xylene, 1-iodo-3-(trifluoromethoxy)benzene, 1-iodo-4-(trifluoromethoxy)benzene, 2-iodobiphenyl, 3-iodobiphenyl, 4-iodobiphenyl, 1-iodonaphthalene, 2-iodonaphthalene, 1-iodo-2-methylnaphthalene and 1-iodo-4-methylnaphthalene; and aryl fluorides such as fluorobenzene, o-fluoroanisole, m-fluoroanisole, p-fluoroanisole, o-fluorotoluene, m-fluorotoluene, p-fluorotoluene, o-fluorophenol, m-fluorophenol, p-fluorophenol, 2-fluorobenzotrifluoride, 3-fluorobenzotrifluoride, 4-fluorobenzotrifluoride, 1-fluoro-2,4-dimethoxybenzene, 1-fluoro-2,5-dimethoxybenzene, 2-fluorophenethyl alcohol, 3-fluorophenethyl alcohol, 4-fluorophenethyl alcohol, 5-fluoro-1,2,4-trimethylbenzene, 2-fluoro-m-xylene, 2-fluoro-p-xylene, 3-fluoro-o-xylene, 4-fluoro-o-xylene, 4-fluoro-m-xylene, 5-fluoro-m-xylene, 1-fluoro-3-(trifluoromethoxy)benzene, 1-fluoro-4-(trifluoromethoxy)benzene, 2-fluorobiphenyl, 3-fluorobiphenyl, 4-fluorobiphenyl, 4-fluoro-1,2-(methylenedioxy)benzene, 1-fluoronaphthalene, 2-fluoronaphthalene, 1-fluoro-2-methylnaphthalene and 1-fluoro-4-methylnaphthalene.

Of the heterocyclic aromatic halides, those which have at least one nitrogen atom as the heteroatom or heteroatoms in the heterocyclic aromatic ring of said halides are preferable. The number of nitrogen atom as the heteroatom or heteroatoms in the heterocyclic aromatic halides is not particularly limited, and is usually in the range of 1 to 10.

The aryl halides used in the process of the invention further include those which have two or more halogen atoms, such as 1,2-dibromobenzene, 1,3-dibromobenzene, 1,4-dibromobenzene, 9,10-dibromoanthracene, 9,10-dichloroanthracene, 4,4'-dibromobiphenyl, 4,4'-dichlorobiphenyl, 4,4'-diiodobiphenyl, 1-bromo-2-fluorobenzene, 1-bromo-3-fluorobenzene, 1-bromo-4-fluorobenzene, 2-bromochlorobenzene, 3-bromochlorobenzene, 4-bromochlorobenzene, 2-bromo-5-chlorotoluene, 3-bromo-4-chlorobenzotrifluoride, 5-bromo-2-chlorobenzotrifluoride, 1-bromo-2,3-dichlorobenzene, 1-bromo-2,6-dichlorobenzene, 1-bromo-3,5-dichlorobenzene, 2-bromo-4-fluorotoluene, 2-bromo-5-fluorotoluene, 3-bromo-4-fluorotoluene, 4-bromo-2-fluorotoluene and 4-bromo-3-fluorotoluene.

The amine compound used in the process of the invention includes primary amines, secondary amines and metal amides.

The primary amines are not particularly limited, and, as specific examples thereof, there can be mentioned aliphatic primary amines such as ethylamine, propylamine, butylamine, isobutylamine, tert.-butylamine, pentylamine, cyclopentylamine, hexylamine, cyclohexylamine, heptylamine and octylamine; and aromatic primary amines such as aniline, o-fluoroaniline, m-fluoroaniline, p-fluoroaniline, o-anisidine, m-anisidine, p-anisidine, o-toluidine, m-toluidine, p-toluidine, 2-naphthylamine, 2-aminobiphenyl and 4-aminobiphenyl.

The secondary amines also are not particularly limited, and, as specific examples thereof, there can be mentioned cyclic secondary amines such as piperazine, 2-methylpiperazine, homopiperazine, N-methylhomopiperazine, 2,6-dimethylpiperazine, N-methylpiperazine, N-ethylpiperazine, N-ethoxycarbonylpiperazine, N-benzylpiperazine, morpholine, 2,6-dimethylmorpholine, piperidine, 2,6-dimethylpiperidine, 3,3-dimethylpiperidine, 3,5-dimethylpiperidine, 2-ethylpiperidine, 4-piperidone ethylene ketal, pyrrolidine and 2,5-dimethylpyrrolidine; and acyclic secondary amines such as dimethylamine, diethylamine, and aromatic ring-containing acyclic secondary amines such as N-methylaniline, N-ethylaniline, N-methylbenzylamine, N-methylphenetylamine and diphenylamine, which may have one or more substituents on the aromatic ring.

The metal amides also are not particularly limited, and includes, for example, aminotin compounds and aminoborane compounds. These metal amides can be synthesized by known processes. For example, aminotin compounds are synthesized by heating (N,N-diethylamino)tributyltin and a corresponding primary amine or secondary amine in toluene in an argon atmosphere. Aminoborane compounds are synthesized from tris(diethylamino)borane and a corresponding primary amine or secondary amine.

In the process of the invention for producing a heterocyclic aromatic amine, the amine compound is allowed to exist in the reaction system usually in an amount in the range of 0.1 mole to a large excess per mole of the heterocyclic aromatic halide, or in the range of 0.1 mole to a large excess per mole of the halogen atom on the ring of the heterocyclic aromatic halide. Unreacted amine compounds are troublesome to recover, and therefore, the amount of the amine compound is preferably in the range of 1 mole to 30 moles per mole of the heterocyclic aromatic halide or in the range of 1 mole to 60 moles per mole of the halogen atom on the ring of the heterocyclic aromatic halide.

In the process of the invention for producing an arylamine, the amine compound is allowed to exist in the reaction system usually in an amount in the range of 0.1 mole to a large excess per mole of the aryl halide, or in the range of 0.1 mole to a large excess per mole of the halogen atom on the ring of the aryl halide. Unreacted amine compounds are troublesome to recover, and therefore, the amount of the amine compound is used preferably in the range of 1 mole to 30 moles per mole of the aryl halide or in the range of 1 mole to 60 moles per mole of the halogen atom on the ring of the aryl halide.

The palladium compound used in the process of the invention is not particularly limited, and, as specific examples of the palladium compound, there can be mentioned tetravalent palladium compounds such as sodium hexachloropalladate(IV) tetrahydrate and potassium hexachloropalladate(IV) tetrahydrate, divalent palladium compounds such as palladium(II) chloride, palladium(II) bromide, palladium(II) acetate, palladium(II) acetylacetonate, dichlorobis(benzonitrile)palladium(II), dichlorobis(acetonitrile)palladium(II), dichlorobis(triphenylphosphine)palladium(II), dichlorotetraamminepalladium(II), dichlorobis(cycloocta-1,5-diene)palladium(II) and palladium(II) trifluoroacetate, and zero-valent palladium compounds such as tris(dibenzylideneacetone)dipalladium(0), tris(dibenzylideneacetone)dipalladium(0) chloroform complex and tetrakis(triphenylphosphine)palladium(0).

In the process of the invention for producing a heterocyclic aromatic amine, the amount of the palladium compound is not particularly limited, but is usually in the range of 0.000001 to 20% by mole expressed in terms of palladium per mole of the heterocyclic aromatic halide. When the amount of the palladium compound is in this range, the heterocyclic aromatic amine can be produced at a high selectivity. In consideration of the enhanced catalyst activity and cost, the palladium compound is preferably used in an amount of 0.0001 to 5% by mole expressed in terms of palladium per mole of the heterocyclic aromatic halide.

Similarly, in the process of the invention for producing an arylamine, the amount of the palladium compound is not particularly limited, but is usually in the range of 0.000001 to 20% by mole expressed in terms of palladium per mole of the aryl halide. When the amount of the palladium compound is in this range, the arylamine can be produced at a high selectivity. In consideration of the enhanced catalyst activity and cost, the palladium compound is preferably used in an amount of 0.0001 to 5% by mole expressed in terms of palladium per mole of the aryl halide.

In the process of the invention for producing a heterocyclic aromatic amine, the tertiary phosphine used in combination with the palladium compound is not particularly limited. As specific examples of the tertiary phosphine, there can be mentioned trialkylphosphines such as triethylphosphine, tri-cyclohexylphosphine, tri-isopropylphosphine, tri-n-butylphosphine, tri-isobutylphosphine, tri-sec-butylphosphine and tri-tert-butylphosphine; triarylphosphines such as triphenylphosphine, tri-pentafluorophenylphosphine, tri-o-tolylphosphine, tri-m-tolylphosphine and tri-p-tolylphosphine; and phenoxyphosphines such as tri-(2,6-dimethylphenoxy)phosphine, tri-(2-tert.-butylphenoxy)phosphine, triphenoxyphospshine, tri(4-methylphenoxy)phospshine and tri(2-methylphenoxy)phospshine.

To enhance the conversion of the heterocyclic aromatic halide, the tertiary phosphine preferably has a cone angle of at least 160°. By the term "cone angle" used herein we mean the cone angle reported by Tolman et al as a measure of the steric effect of phosphine [Chem. Rev., 77, 313 (1977)]. As examples of the preferable tertiary phosphine having a cone angle of at least 160°, there can be mentioned tri-tert.-butylphosphine, tri-(2,6-dimethylphenoxy)phosphine, tri-o-tolylphosphine, tri-cyclohexylphosphine and tri-isopropylphosphine. To enhance the selectivity to the heterocyclic aromatic amine, the tertiary phosphine preferably has a cone angle of 160 to 190°. As an specific example of such tertiary phosphine, there can be mentioned tri-tert.-butylphosphine.

In the process of the invention for producing an arylamine, the trialkylphosphine used in combination with the palladium compound is not particularly limited. As specific examples of the trialkylphosphine, there can be mentioned triethylphosphine, tri-cyclohexylphosphine, tri-isopropylphosphine, tri-n-butylphosphine, tri-isobutylphosphine, tri-sec-butylphosphine and tri-tert.-butylphosphine. Of these, tri-tert.-butylphosphine is most preferable in view of the highest selectivity to the arylamine.

In the process of the invention for producing a heterocyclic aromatic amine, the tertiary phosphine is used usually in an amount of 0.01 to 10000 moles per mole of the palladium compound. When the amount of the tertiary phosphine is in this range, a good selectivity to the heterocyclic aromatic amine can be obtained. In consideration of the enhanced conversion and cost, the amount of the tertiary phosphine is preferably 0.1 to 10 moles per mole of the palladium compound.

Similarly, in the process of the invention for producing an arylamine, the trialkylphosphine is used usually in an amount of 0.01 to 10000 moles per mole of the palladium compound. When the amount of the trialkylphosphine is in this range, a good selectivity to the arylamine can be obtained. In consideration of the enhanced conversion and cost, the amount of the trialkylphosphine is preferably 0.1 to 10 moles per mole of the palladium compound.

In the process of the invention, it is indispensable to use a palladium compound in combination with a tertiary phosphine or a trialkylphosphine as the catalyst. These catalyst ingredients can be incorporated in the reaction system either as they are alone, or in the form of a complex which has been previously prepared by reacting a palladium compound with a tertiary phosphine or a trialkylphosphine.

The base used in the process of the invention is not particularly limited and can be selected from organic bases and inorganic bases. The base may be used either alone or in combination. As preferable examples of the base, there can be mentioned alkali metal alkoxides such as sodium methoxide, sodium ethoxide, potassium methoxide, potassium ethoxide, lithium tert.-butoxide, sodium tert.-butoxide and potassium tert.-butoxide. These metal alkoxides can be either added as they are or synthesized in-situ from an alkali metal, an alkali metal hydride or an alkali metal hydroxide, and an alcohol.

The amount of the base used is preferably at least 0.5 mole per mole of the hydrogen halide produced by the reaction. If the amount of the base is smaller than 0.5 mole, the yield of the heterocyclic aromatic amine or arylamine tends to be reduced. Even if an excessive amount of the base is used, the yield of the heterocyclic aromatic amine or arylamine is not varied, but a treatment conducted after completion of the reaction becomes troublesome. Therefore, the amount of the base is more preferably 1 to 5 moles per mole of the hydrogen halide.

The amination reaction in the invention is carried out usually in the presence of an inert solvent. The inert solvent used is not particularly limited provided that it does not influence a baneful effect on the reaction. As specific examples of the inert solvent, there can be mentioned aromatic hydrocarbons such as benzene, toluene and xylene; ethers such as diethyl ether, tetrahydrofuran and dioxane; and acetonitrile, dimethylformamide, dimethylsulfoxide and hexamethylphosphotriamide. Of these, aromatic hydrocarbons such as benzene, toluene and xylene are preferable.

The amination reaction can be conducted either under normal pressure in an atmosphere of an inert gas such as argon or nitrogen, or under a high pressure. The reaction temperature is usually in the range of 20 to 300° C., preferably 50 to 200° C.

The reaction time varies depending upon the particular amounts of the heterocyclic aromatic halide or aryl halide, amine compound, base, palladium compound, tertiary phosphine or trialkylphosphine, and the particular reaction temperature, and is usually in the range of several minutes to 72 hours.

After completion of the amination reaction, the intended compound can be recovered and treated by the conventional procedure.

The invention will now be specifically described by the following examples that by no means limit the scope of the invention.

The yields in the examples were calculated on the basis of the aryl halide or heterocyclic aromatic halide charged.

Reference Example 1 (Preparation of Catalyst 1)

A 100 ml Kjeldahl flask was charged with 97 mg of tris(dibenzylideneacetone)dipalladium (supplied by Aldrich) and 10 ml of o-xylene at room temperature in a nitrogen atmosphere. Tri-tert.-butylphosphine (supplied by Kanto Kagaku K.K.) was added to the content in the flask while being stirred, and maintained at 60° C. for 10 minutes in an oil bath while being stirred, to give a catalyst. The amount of the tri-tert.-butylphosphine was such that the ratio of tri-tert.-butylphosphine/Pd was 4/1 by mole.

Reference Example 2 (Preparation of Catalyst 2)

By the known method described in J. Organomet. Chem., 65, 253 (1974), tris(dibenzylideneacetone)dipalladium-chloroform complex was synthesized. Using 104 mg of this complex, a catalyst was prepared by the same procedure as employed in Reference Example 1.

Reference Example 3 (Preparation of Catalyst 3)

A 100 ml Kjeldahl flask was charged with 97 mg of tris(dibenzylideneacetone)dipalladium (supplied by Aldrich) and 10 ml of o-xylene at room temperature in a nitrogen atmosphere. 265 mg of tri-o-tolylphosphine was added to the content in the flask while being stirred, and maintained at 60° C. for 10 minutes in an oil bath while being stirred, to give a catalyst.

Example 1

A dropping funnel was charged with about 10 ml of a solution in o-xylene of catalyst 1 prepared in Reference Example 1 (the ratio of palladium atom/heterocyclic aromatic halide=0.5% by mole). A 200 ml Kjeldahl flask was equipped with the dropping funnel, a cooling condenser and a thermometer. At room temperature, 22 g of piperazine, 6.72 g of 3-bromopyridine as a heterocyclic aromatic halide (the ratio of piperazine/heterocyclic aromatic halide=6/1 by mole), and 5.66 g of sodium tert.-butoxide (hereinafter abbreviated to "NaOBu$^t$") (the ratio of NaOBu$^t$/heterocyclic aromatic halide=1.38/1 by mole) were separately incorporated into the flask, each as a solution in 20 ml of o-xylene. The flask was flushed with nitrogen for about 20 minutes while the content was stirred, and the content was heated to 80° C. At this temperature, the catalyst solution was dropped into the flask, and the content was heated to 120° C. and maintained at that temperature for 3 hours with stirring.

After completion of the reaction, the content was cooled in an ice-water bath maintained at a temperature of 0 to 10° C., and the thus-formed precipitate was filtered off. The mother liquor was concentrated to remove the solvent, and then distilled at a temperature of 123 to 127° C. under a reduced pressure of 1 mmHg to give colorless oily 1-(3-pyridyl)piperazine. The yield was 82% by mole.

Example 2

By the same procedures as those described in Example 1, colorless oily 1-(3-pyridyl)piperazine was obtained wherein a solution of catalyst 2, prepared in Reference Example 2, in about 10 ml of o-xylene (the ratio of palladium atom/heterocyclic aromatic halide=0.5% by mole) was used with all other conditions remaining the same. The yied was 85% by mole Example 3

By the same procedures as those described in Example 1, colorless oily 1-(3-pyridyl)piperazine was obtained wherein catalyst 3, prepared in Reference Example 3, was used with all other conditions remaining the same. The yield was 72% by mole.

Example 4

A 200 ml Kjeldahl flask equipped with a cooling condenser and a thermometer was charged with a solution of 22 g of piperazine in 20 ml of o-xylene, a solution of 6.72 g of 3-bromopyridine in 20 ml of o-xylene and a solution of 5.66 g of NaOBu$^t$ in 20 ml of o-xylene, and further with a solution of 48 mg of palladium acetate in 15 ml of o-xylene (the ratio of palladium atom/heterocyclic aromatic halide= 0.5% by mole). The flask was flushed with nitrogen for about 20 minutes while the content was stirred, and 0.2 ml of tri-tert.-butylphosphine was added. Then the mixture was heated to 120° C., and maintained at that temperature for 3 hours with stirring. After completion of the reaction, the same treatment as employed in Example 1 was conducted to give colorless oily 1-(3-pyridyl)piperazine. The yield was 86% by mole.

Example 5

By the same procedures as those described in Example 4, 1-(3-pyridyl)piperazine was obtained wherein 38 mg of palladium chloride was used instead of 48 mg of palladium acetate with all other conditions remaining the same. The yield was 73% by mole.

Example 6

A 500 ml Kjeldahl flask equipped with a cooling condenser and a thermometer was charged with a solution of 44.6 g of piperazine in 45 ml of o-xylene, a solution of 13.44 g of 3-bromopyridine in 45 ml of o-xylene, and a solution of 11.3 g of NaOBu$^t$ in 45 ml of o-xylene, and further with a solution of 19 mg of palladium acetate in 10 ml of o-xylene (the ratio of palladium atom/heterocyclic aromatic halide=0.1% by mole). The flask was flushed with nitrogen for about 20 minutes while the content was stirred, and 0.26 ml of a solution in toluene of tri-tert.-butylphosphine having a concentration of 0.256 g/ml was added. Then the mixture was heated to 120° C., and maintained at that temperature for 3 hours with stirring. After completion of the reaction, the same treatment as employed in Example 1 was conducted to give colorless oily 1-(3-pyridyl)piperazine. The yield was 86% by mole.

Example 7

By the same procedures as those described in Example 6, 1-(3-pyridyl)piperazine was obtained wherein the amount of palladium acetate was changed to 4.8 mg (the ratio of palladium atom/heterocyclic aromatic halide=0.025% by mole) with all other conditions remaining the same. The yield was 82% by mole.

Example 8

A 200 ml Kjeldahl flask equipped with a cooling condenser and a thermometer was charged with a solution of 22 g of piperazine in 20 ml of o-xylene, a solution of 8.88 g of 3-bromoquinoline in 20 ml of o-xylene, and a solution of 5.66 g of NaOBu$^t$ in 20 ml of o-xylene, and further with a solution of 4.9 mg of palladium acetate in 15 ml of o-xylene (the ratio of palladium atom/heterocyclic aromatic halide=0.05% by mole). The flask was flushed with nitrogen for about 20 minutes while the content was stirred, and 0.07 ml of a solution in toluene of tri-tert.-butylphosphine having a concentration of 0.237 g/ml was added. Then the mixture was heated to 120° C., and maintained at that temperature for 3 hours with stirring. After completion of the reaction, the reaction product was extracted with 80 ml of water and then the thus-formed aqueous phase was extracted twice with 80 ml of ethyl acetate. The thus-obtained organic phase was concentrated, dried in vacuum, and then recrystallized from cyclohexane to give 7.1 g of yellow solid 3-(1-piperazinyl)quinoline (purity: 93%). The yield was 73% by mole.

Example 9

In a suspension of 26.6 g of KOH in 200 ml of dimethylformamide, 20.1 g of solid 5-bromoindole was incorporated while being stirred. The mixture was stirred for 50 minutes at room temperature, and 25.4 g of benzyl chloride was dropwise added to the mixture over a period of 16 minutes at a temperature of not higher than 30° C. The reaction mixture was maintained at 30° C. in an oil bath for 5 hours with stirring. After completion of the reaction, 200 ml of water was added and the thus-formed aqueous phase was extracted with 120 ml of ether three times. The thus-obtained organic phase was washed with water and dried over sodium sulfate overnight. The dried product was concentrated to dryness and then recrystallized from isopropyl ether to give 23.5 g of N-benzyl-5-bromoindole. The yield was 80% by mole.

A flask was charged with 75 ml of o-xylene, 6.21 g of N-benzyl-5-bromoindole, 11.2 g of piperazine and 2.85 g of NaOBu$^t$. The flask was flushed with nitrogen for 10 minutes, and then, 6.0 mg of palladium acetate (the ratio of palladium atom/N-benzyl-5-bromoindole=0.10% by mole) and 0.07 ml of a solution in toluene of tri-tert.-butylphosphine having a concentration of 0.25 g/ml were added into the flask. Then the content was heated to 110° C. and maintained at that temperature for 3 hours. Extraction, drying and concentration were conducted, and finally recrystallization was conducted from toluene to give N-benzyl-5-(1-piperazinyl)indole. The yield was 89% by mole on the basis of N-benzyl-5-bromoindole.

Comparative Example 1

A 200 ml Kjeldahl flask equipped with a cooling condenser and a thermometer was charged at room temperature with 22 g of piperazine, 6.72 g of 3-bromopyridine (the ratio of piperazine/heterocyclic aromatic halide=6/1 by mole) and 2.4 g of copper(I) iodide (the ratio of copper iodide/heterocyclic aromatic halide=30% by mole), and further with 75 ml of dimethylformamide. The content was refluxed for 3 hours in a nitrogen atmosphere. The liquid reaction product was cooled to room temperature, and then filtered. Gas chromatographic analysis of the thus-obtained mother liquor revealed that the conversion of the starting 3-bromopyridine was 25% by mole and the yield of 1-(3-pyridyl)piperazine was 17% by mole.

Example 10

A dropping funnel was charged with about 10 ml of a solution in o-xylene of catalyst 1 prepared in Reference Example 1 (the ratio of palladium atom/aryl halide=0.5% by mole). A 200 ml Kjeldahl flask was equipped with the dropping funnel, a cooling condenser and a thermometer. At room temperature, 22 g of piperazine, 7.99 g of m-bromoanisole as an aryl halide (the ratio of piperazine/aryl halide=6/1 by mole), and 5.66 g of NaOBu$^t$ (the ratio of NaOBu$^t$/aryl halide=1.38/1 by mole) were separately incorporated into the flask, each as a solution in 20 ml of o-xylene. The flask was flushed with nitrogen for about 20 minutes while the content was stirred, and the content was heated to 80° C. At this temperature, the catalyst solution was dropped into the flask, and the content was heated to 120° C. and maintained at that temperature for 3 hours with stirring.

After completion of the reaction, 80 ml of water was added to cool the reaction product. The liquid reaction product was incorporated in a separatory funnel and the organic phase was separated. Thus-obtained aqueous phase was extracted with 40 ml of o-xylene. The organic phase was dried over sodium sulfate. Gas chromatographic analysis of the dried product by the internal standard method revealed that the intended arylamine, i.e., N-(3-methoxyphenyl)piperazine was obtained in a yield of 96% by mole.

Example 11

The procedures as described in Example 10 were repeated wherein 7.99 g of p-bromoanisole was used as the aryl halide instead of 7.99 g of m-bromoanisole with all other conditions remaining the same. The results are shown in Table 1.

Example 12

The procedures as described in Example 10 were repeated wherein 7.47 g of 1-bromo-4-fluorobenzene was used as the aryl halide instead of 7.99 g of m-bromoanisole with all other conditions remaining the same. The results are shown in Table 1.

Example 13

The procedures as described in Example 10 were repeated wherein 7.31 g of o-bromotoluene was used as the aryl halide instead of 7.99 g of m-bromoanisole with all other conditions remaining the same. The results are shown in Table 1.

Example 14

The procedures as described in Example 10 were repeated wherein 7.31 g of m-bromotoluene was used as the aryl halide instead of 7.99 g of m-bromoanisole with all other conditions remaining the same. The results are shown in Table 1.

Example 15

The procedures as described in Example 10 were repeated wherein 6.92 g of bromobenzene was used as the aryl halide instead of 7.99 g of m-bromoanisole with all other conditions remaining the same. The results are shown in Table 1.

TABLE 1

| Example | Aryl halide | Arylamine | Yield (mole %) |
|---------|-------------|-----------|----------------|
| 11 | CH₃O—⟨ ⟩—Br | CH₃O—⟨ ⟩—N(piperazine)NH | 84 |
| 12 | F—⟨ ⟩—Br | F—⟨ ⟩—N(piperazine)NH | 91 |
| 13 | 2-CH₃-C₆H₄—Br | 2-CH₃-C₆H₄—N(piperazine)NH | 92 |
| 14 | 3-CH₃-C₆H₄—Br | 3-CH₃-C₆H₄—N(piperazine)NH | 92 |
| 15 | C₆H₅—Br | C₆H₅—N(piperazine)NH | 89 |

Comparative Example 2

A 100 ml Kjeldahl flask was charged with 97 mg of tris(dibenzylideneacetone)dipalladium (supplied by Aldrich) and 10 ml of o-xylene at room temperature in a nitrogen atmosphere. 265 mg of tri-o-tolylphosphine was added to the content in the flask while being stirred, and maintained at 60° C. for 10 minutes with stirring in an oil, to give a catalyst.

A dropping funnel was charged with about 10 ml of a solution in o-xylene of the thus-prepared catalyst (the ratio of palladium atom/aryl halide=0.5% by mole). A 200 ml Kjeldahl flask was equipped with the dropping funnel, a cooling condenser and a thermometer. At room temperature, 22 g of piperazine, 7.99 g of m-bromoanisole as an aryl halide and 5.67 g of NaOBu$^t$ were separately incorporated into the flask, each as a solution in 20 ml of o-xylene. The flask was flushed with nitrogen for about 20 minutes with stirring, and the content was heated to 80° C. At this temperature, the catalyst solution was dropwise added into the flask, and the content was heated to 120° C. and maintained at that temperature for 3 hours with stirring.

After completion of the reaction, the content was cooled by adding 80 ml of water. Then the reaction product was introduced in a separatory funnel and the organic phase was separated. The lower aqueous phase was extracted with 40 ml of o-xylene. The organic phase was dried over sodium sulfate. Gas chromatographic analysis of the dried product by the internal standard method revealed that the intended arylamine, i.e., N-(3-methoxyphenyl)piperazine was obtained in a yield shown in Table 2.

Comparative Example 3

The procedures employed in Comparative Example 2 were repeated wherein 7.99 g of p-bromoanisole was used as an aryl halide instead of 7.99 g of m-bromoanisole with all other conditions remaining the same. Gas chromatographic analysis of the obtained product by the internal standard method revealed that the intended arylamine, i.e., N-(4-methoxyphenyl)piperazine was obtained in a yield shown in Table 2.

Comparative Example 4

The procedures employed in Comparative Example 2 were repeated wherein a catalyst was prepared from 19.7 mg of tris(dibenzylideneacetone)dipalladium (supplied by Aldrich) and 54.6 mg of tri-o-tolylphosphine, and 7.47 g of 1-bromo-4-fluorobenzene (the ratio of palladium atom/aryl halide=0.1% by mole) was used as an aryl halide instead of 7.99 g of m-bromoanisole with all other conditions remaining the same. Gas chromatographic analysis of the obtained product by the internal standard method revealed that the intended arylamine, i.e., N-(4-fluorophenyl)piperazine was obtained in a yield shown in Table 2.

Comparative Example 5

The procedures employed in Comparative Example 2 were repeated wherein a catalyst was prepared from 19.7 mg of tris(dibenzylideneacetone)dipalladium (supplied by Aldrich) and 54.6 mg of tri-o-tolylphosphine, and 7.30 g of o-bromotoluene (the ratio of palladium atom/aryl halide= 0.1% by mole) was used as an aryl halide instead of 7.99 g of m-bromoanisole with all other conditions remaining the same. Gas chromatographic analysis of the obtained product by the internal standard method revealed that the intended arylamine, i.e., N-(o-tolyl)piperazine was obtained in a yield shown in Table 2.

Comparative Example 6

The procedures employed in Comparative Example 2 were repeated wherein a catalyst was prepared from 19.7 mg of tris(dibenzylideneacetone)dipalladium (supplied by Aldrich) and 54.6 mg of tri-o-tolylphosphine, and 7.99 g of o-bromoanisole (the ratio of palladium atom/aryl halide= 0.1% by mole) was used as an aryl halide instead of 7.99 g of m-bromoanisole with all other conditions remaining the same. Gas chromatographic analysis of the obtained product by the internal standard method revealed that the intended arylamine, i.e., N-(o-methoxyphenyl)piperazine was obtained in a yield shown in Table 2.

Comparative Example 7

A 100 ml Kjeldahl flask equipped with a cooling condenser and a thermometer was charged with 96 mg of tris(dibenzylideneacetone)dipalladium (supplied by Aldrich) and 10 ml of o-xylene at room temperature in a nitrogen atmosphere. 257 mg of tri-o-tolylphosphine was added to the content in the flask while being stirred, and maintained at 60° C. for 10 minutes with stirring in an oil, to give a catalyst. The content was then cooled to room temperature, and, in a nitrogen atmosphere, 1.36 g of 2-methylpiperazine, 2.0 g of m-bromoanisole as an aryl halide (the ratio of palladium atom/aryl halide=2.0% by mole) and 1.43 g of NaOBu$^t$ were separately incorporated into the flask, each as a solution in 10 ml of o-xylene. The content in the flask was to 100° C. and maintained at that temperature for 3 hours with stirring.

After completion of the reaction, the content was concentrated, water was added to the residue, and then, the mixture was extracted with ethyl acetate. The liquid extract was concentrated and dried in vacuum overnight to give brown oily N-(3-methoxyphenyl)-2-methylpiperazine. The result of the gas chromatographic analysis of the product is shown in Table 2.

Comparative Example 8

The procedures employed in Comparative Example 7 were repeated wherein 1.29 g of N-methylpiperazine was used instead of 1.36 g of 2-methylpiperazine with all other conditions remaining the same. Brown oily N-methyl, N'-(3-methoxyphenyl)piperazine was obtained. The result of gas chromatographic analysis of the product is shown in Table 2.

TABLE 2

| Comparative Example | Arylamine | Yield (mole %) |
|---|---|---|
| 2 | 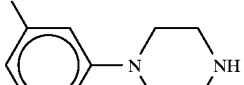 | 61 |
| 3 | 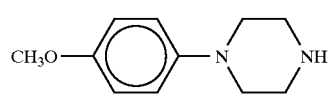 | 40 |

TABLE 2-continued

| Comparative Example | Arylamine | Yield (mole %) |
|---|---|---|
| 4 | 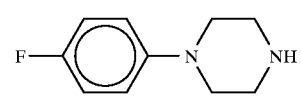 | 7 |
| 5 | 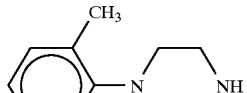 | 5 |
| 6 | 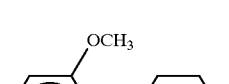 | 3 |
| 7 | 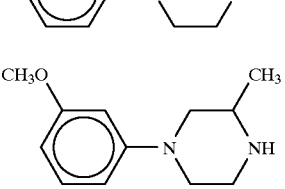 | 72 |
| 8 | 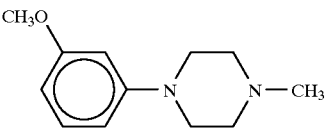 | 42 |

Example 16

The procedures employed in Example 10 were repeated wherein 4.78 g of chlorobenzene (the ratio of palladium atom/aryl halide=0.5% by mole) was used instead of 7.99 g of m-bromoanisole as an aryl halide with all other conditions remaining the same. Gas chromatographic analysis of the obtained product by the internal standard method revealed that the intended arylamine, i.e., N-phenylpiperazine was obtained in a yield of 94% by mole.

Example 17

The procedures employed in Example 10 were repeated wherein 9.99 g of m-iodoanisole (the ratio of palladium atom/aryl halide=0.5% by mole) was used instead of 7.99 g of m-bromoanisole as an aryl halide with all other conditions remaining the same. Gas chromatographic analysis of the obtained product by the internal standard method revealed that the intended arylamine, i.e., N-(3-methoxyphenyl) piperazine was obtained in a yield of 88% by mole.

Example 18

A dropping funnel was charged with about 10 ml of a solution in o-xylene of catalyst 1 prepared in Reference Example 1 (the ratio of palladium atom/aryl halide=0.5% by mole). A 200 ml Kjeldahl flask was equipped with the dropping funnel, a cooling condenser and a thermometer. At room temperature, 4.71 g of piperidine as an amine compound, 7.99 g of m-bromoanisole as an aryl halide (the ratio of amine compound/aryl halide=1.2/1 by mole), and 5.67 g of NaOBu$^t$ were separately incorporated into the flask, each as a solution in 20 ml of o-xylene. The flask was flushed with nitrogen for about 10 minutes while the content was stirred, and the content was heated to 80° C. At this temperature, the catalyst solution was dropped into the flask, and the content was heated to 105° C. and maintained at that temperature for 3 hours with stirring.

After completion of the reaction, 80 ml of water was added to cool the reaction product. The liquid reaction product was incorporated in a separatory funnel and the organic phase was separated. Thus-obtained aqueous phase was extracted with 40 ml of o-xylene. The organic phase was dried over sodium sulfate, concentrated and then distilled to give a light yellow oily N-(3-methoxyphenyl)piperidine. The yield of the isolated compound was 97% by mole.

Example 19

The procedures employed in Example 18 were repeated wherein 5.13 g of N-methylpiperazine was used instead of 4.71 g of piperidine as an amine compound with all other conditions remaining the same. Light yellow oily N-methyl, N'-(3-methoxyphenyl)piperazine was obtained. The yield of the isolated compound is shown in Table 3.

Example 20

The procedures employed in Example 18 were repeated wherein 4.48 g of morpholine was used instead of 4.71 g of piperidine as an amine compound, and catalyst 2 prepared in in Reference Example 2 (the ratio of palladium atom/aryl halide=0.5% by mole) was used instead of catalyst 1, with all other conditions remaining the same. Light yellow oily N-(3-methoxyphenyl)morpholine was obtained. The yield of the isolated compound is shown in Table 3.

Example 21

The procedures employed in Example 18 were repeated wherein 5.49 g of N-methylaniline was used instead of 4.71 g of piperidine as an amine compound with all other conditions remaining the same. Light yellow oily N-methyl, N-(3-methoxyphenyl)aniline was obtained. The yield of the isolated compound is shown in Table 3.

Example 22

The procedures employed in Example 18 were repeated wherein 6.71 g of N-methylbenzylamine was used instead of 4.71 g of piperidine as an amine compound, and the o-xylene phase containing the reaction product was concentrated and then dried in vacuum for 15 hours, with all other conditions remaining the same. Brown yellow oily N-methyl, N-(3-methoxyphenyl)benzylamine was obtained. The yield as measured by gas chromatographic analysis is shown in Table 3.

Example 23

The procedures employed in Example 18 were repeated wherein 7.90 g of N-piperidone ethylene ketal was used instead of 4.71 g of piperidine as an amine compound, and the o-xylene phase containing the reaction product was concentrated and then dried in vacuum for 15 hours, with all other conditions remaining the same. Brown yellow oily N-(3-methoxyphenyl)-4-piperidone ethylene ketal was obtained. The yield as measured by gas chromatographic analysis is shown in Table 3.

Example 24

The procedures employed in Example 18 were repeated wherein 6.00 g of N-fluoroaniline was used instead of 4.71 g of piperazine as an amine compound, catalyst 2 prepared in Reference Example 2 was used instead of catalyst 1, with all other conditions remaining the same, and the o-xylene phase containing the reaction product was concentrated and then dried in vacuum for 15 hours. Dark brown solid N-(3-methoxyphenyl)-p-fluoroaniline was obtained. The yield as measured by gas chromatographic analysis is shown in Table 3.

TABLE 3

| Example | Aryl halide | Arylamine | Yield (mole %) |
|---|---|---|---|
| 19 | HN(CH2CH2)2N—CH3 | CH3O-C6H4-N(CH2CH2)2N—CH3 | 89 |
| 20 | HN(CH2CH2)2O (morpholine) | CH3O-C6H4-N(CH2CH2)2O | 93 |
| 21 | HN(Ph)(CH3) | CH3O-C6H4-N(Ph)(CH3) | 97 |
| 22 | HN(Bn)(CH3) | CH3O-C6H4-N(Bn)(CH3) | 96 |
| 23 | HN-piperidone ethylene ketal | CH3O-C6H4-N-piperidone ethylene ketal | 95 |

TABLE 3-continued

| Example | Aryl halide | Arylamine | Yield (mole %) |
|---|---|---|---|
| 24 | H₂N—⟨phenyl⟩—F | CH₃O—⟨phenyl⟩—N(H)—⟨phenyl⟩—F | 97 |

Ph: Phenyl group
Bn: Benzyl group

Example 25

A 200 ml Kjeldahl flask equipped with a cooling condenser and a thermometer was charged with a solution of 4.72 g of piperidine in 20 ml of o-xylene, a solution of 7.99 g of m-bromoanisole in 20 ml of o-xylene, and a solution of 5.66 g of NaOBu$^t$ in 20 ml of o-xylene, and further with a solution of 48 mg of palladium acetate in 5 ml of o-xylene (the ratio of palladium atom/m-bromoanisole=0.5% by mole). The flask was flushed with nitrogen for about 20 minutes while the content was stirred, and 0.2 ml of tri-tert.-butylphosphine was added. Then the mixture was heated to 105° C., and maintained at that temperature for 3 hours with stirring. After completion of the reaction, 80 ml of water was added to cool the reaction product. The mixture was introduced in a separatory funnel and the organic phase was separated. The lower aqueous phase was extracted with 40 ml of o-xylene. The organic phase was dried over sodium sulfate, concentrated, and then distilled to give N-(3-methoxyphenyl)piperidine. The yield of the isolated compound was 95% by mole.

Example 26

A 200 ml Kjeldahl flask equipped with a cooling condenser and a thermometer was charged with a solution of 22.0 g of piperazine in 20 ml of o-xylene, a solution of 7.47 g of 1-bromo-4-fluorobenzene in 20 ml of o-xylene, and a solution of 5.66 g of NaOBu$^t$ in 20 ml of o-xylene, and further with a solution of 48 mg of palladium acetate in 5 ml of o-xylene (the ratio of palladium atom/1-bromo-4-fluorobenzene=0.5% by mole). The flask was flushed with nitrogen for about 20 minutes while the content was stirred, and 0.25 ml of tri-tert.-butylphosphine was added. Then the mixture was heated to 120° C., and maintained at that temperature for 3 hours with stirring. After completion of the reaction, 80 ml of water was added to cool the reaction product. The mixture was introduced in a separatory funnel and the organic phase was separated. The lower aqueous phase was extracted with 40 ml of o-xylene. The organic phase was dried over sodium sulfate. Gas chromatographic analysis of the obtained product by the internal standard method revealed that the intended arylamine, i.e., N-(4-fluorophenyl)piperazine was obtained in a yield of 95% by mole.

Example 27

The procedures employed in Example 12 were repeated wherein catalyst 2 prepared in Reference Example 2 (the ratio of palladium/1-bromo-4-fluorobenzene=0.5% by mole) was used with all other conditions remaining the same. The intended N-(4-fluorophenyl)piperazine was obtained in a yield of 92% by mole.

Example 28

A 200 ml Kjeldahl flask equipped with a cooling condenser and a thermometer was charged with a solution of 22.0 g of piperazine in 20 ml of o-xylene, a solution of 6.70 g of bromobenzene in 20 ml of o-xylene, and a solution of 5.66 g of NaOBu$^t$ in 20 ml of o-xylene, and further with a solution of 4.5 mg of palladium acetate in 5 ml of o-xylene (the ratio of palladium atom/bromobenzene=0.05% by mole). The flask was flushed with nitrogen for about 20 minutes while the content was stirred, and 0.2 ml of tri-tert.-butylphosphine was added. Then the mixture was heated to 120° C., and maintained at that temperature for 3 hours with stirring. After completion of the reaction, 80 ml of water was added to cool the reaction product. The mixture was introduced in a separatory funnel and the organic phase was separated. The lower aqueous phase was extracted with 40 ml of o-xylene. The organic phase was dried over sodium sulfate. Gas chromatographic analysis of the obtained product by the internal standard method revealed that the intended arylamine, i.e., N-phenylpiperazine was obtained in a yield of 92% by mole.

Examples 29–31

The procedures employed in Example 28 were repeated wherein aryl halides shown in Table 4 were used instead of bromobenzene with all other conditions remaining the same. The thus-obtained products were further purified to give the intended arylamines in yields shown in Table 4.

TABLE 4

| Example | Aryl halide | Arylamine | Yield (mole %) |
|---|---|---|---|
| 29 | CF₃—⟨phenyl⟩—Br | CF₃—⟨phenyl⟩—N(piperazine)N—H | 82 |

TABLE 4-continued

| Example | Aryl halide | Arylamine | Yield (mole %) |
|---------|-------------|-----------|----------------|
| 30 | Br-[benzodioxole] | H-N(piperazine)N-[benzodioxole] | 84 |
| 31 | Br-[naphthyl] | H-N(piperazine)N-[naphthyl] | 85 |

Example 32

The procedures employed in Example 18 were repeated wherein 6.6 g of potassium tert.-butoxide was used instead of 5.67 g of NaOBu$^t$ with all other conditions remaining the same. N-(3-methoxyphenyl)piperidine was obtained in a yield of 95% by mole.

Example 33

The procedures employed in Example 26 were repeated wherein tri-sec-butylphosphine was used for the preparation of a catalyst instead of tri-tert-butylphosphine with all other conditions remaining the same. N-(4-fluorophenyl)piperazine was obtained in a yield of 82% by mole.

Example 34

The procedures employed in Example 18 were repeated wherein toluene was used instead of o-xylene with all other conditions remaining the same. The yield of isolated N-(3-methoxyphenyl)piperidine was 96% by mole.

Example 35

A 200 ml Kjeldahl flask equipped with a cooling condenser and a thermometer was charged with a solution of 4.37 g (47.0 m-moles) of aniline as an amine compound (the ratio of amine compound/bromine atom in the aryl bromide= 1.1 by mole) in 25 ml of o-xylene, a solution of 9.60 g (42.7 m-moles) of 3-bromobenzotrifluoride as an aryl bromide in 25 ml of o-xylene, and a solution of 5.66 g (58.9 m-mole) of NaOBu$^t$ (the ratio of NaOBu$^t$/bromine atom in the aryl bromide=1.38) in 25 ml of o-xylene, and further with 4.5 mg of palladium acetate (the ratio of palladium atom/aryl bromide=0.05% by mole). The flask was flushed with nitrogen for about 20 minutes while the content was stirred, and tri-tert.-butylphosphine (the ratio of tri-tert.-butylphosphine/palladium acetate=4 by mole) was added. Then the mixture was heated to 120° C., and maintained at that temperature for 3 hours with stirring. After completion of the reaction, 80 ml of water was added to cool the reaction product. The mixture was introduced in a separatory funnel and the organic phase was separated. The lower aqueous phase was extracted with 40 ml of o-xylene. The organic phase was dried over sodium sulfate, concentrated and further dried. The thus-obtained product was treated by a silica gel column chromatography to give the intended arylamine. The obtained arylamine and its yield are shown in Table 5.

Examples 36–48

The procedures employed in Example 35 were repeated wherein amine compounds and aryl bromides shown in Table 5 were used with all other conditions remaining the same. The obtained arylamines and yields thereof are shown in Table 5.

TABLE 5

| Example No. | Aryl bromide | Amine compound |
|-------------|--------------|----------------|
| 36 | 3-CF$_3$-C$_6$H$_4$-Br | NH$_2$-[phenyl] |
| 37 | [biphenyl]-Br | NH$_2$-[phenyl] |

TABLE 5-continued
| 38 | 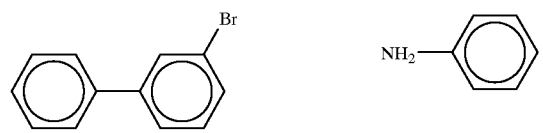 |
| --- | --- |
| 39 | 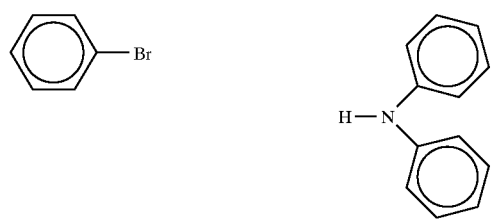 |
| 40 | 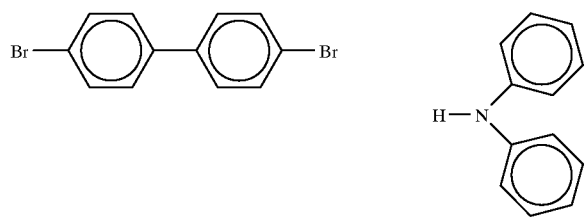 |
| 41 | 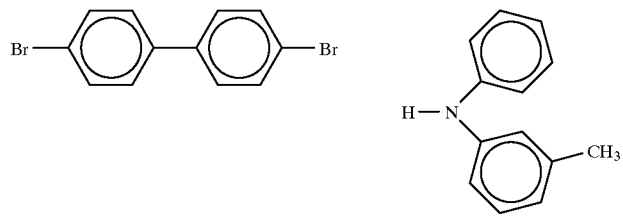 |
| 42 | 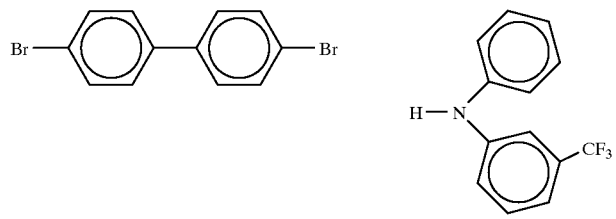 |
| 43 | 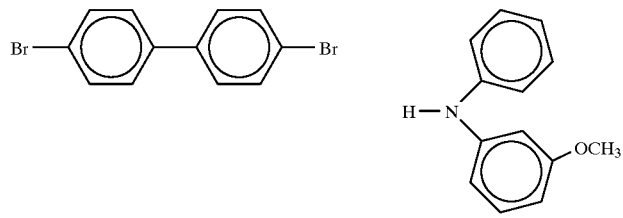 |
| 44 | 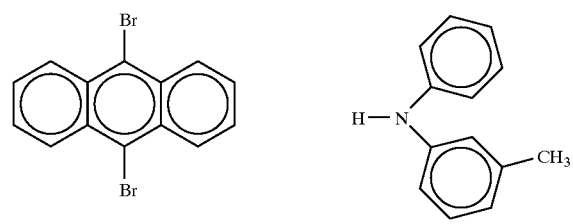 |

TABLE 5-continued

| Example | Aryl halide | Arylamine |
|---|---|---|
| 45 | bromobenzene | N-(3-methylphenyl)aniline |
| 46 | 1,3,5-tribromobenzene | N-(3-methylphenyl)aniline |
| 47 | 2-bromotoluene | N-(3-methylphenyl)aniline |
| 48 | 1,4-dibromobenzene | N-(3-methylphenyl)aniline |

| Example No. | Arylamine | Yield (mole %) |
|---|---|---|
| 36 | N-phenyl-3-(trifluoromethyl)aniline | 93 |
| 37 | N-phenyl-4-biphenylamine | 92 |
| 38 | N-phenyl-3-biphenylamine | 89 |

TABLE 5-continued
| 39 | 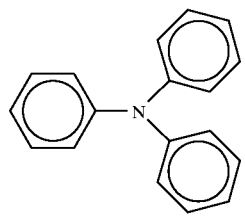 | 96 |
| 40 | 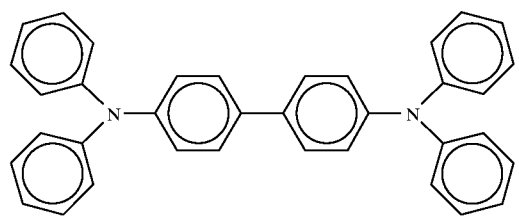 | 96 |
| 41 | 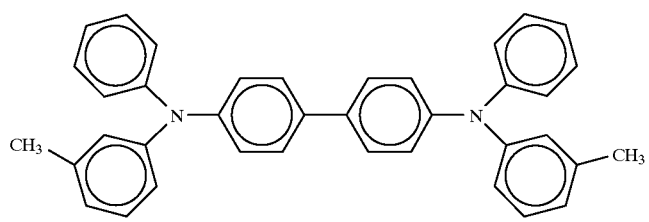 | 91 |
| 42 | 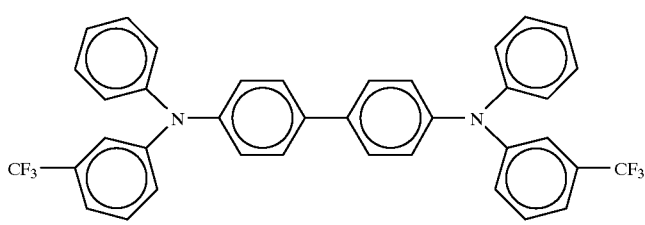 | 94 |
| 43 | 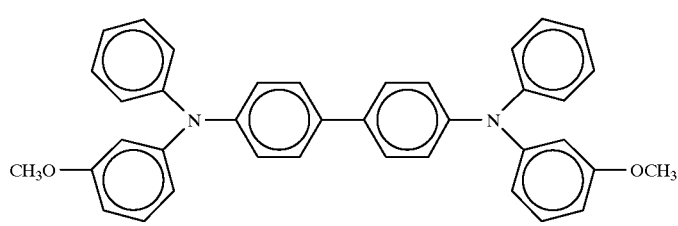 | 93 |
| 44 | 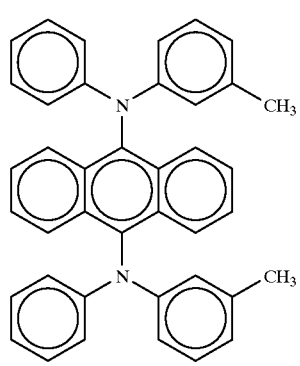 | 86 |

TABLE 5-continued

45 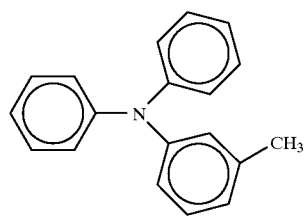 97

46 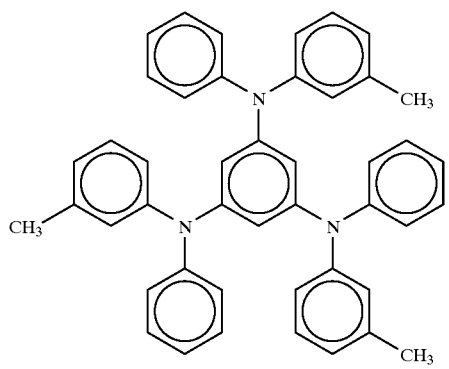 78

47 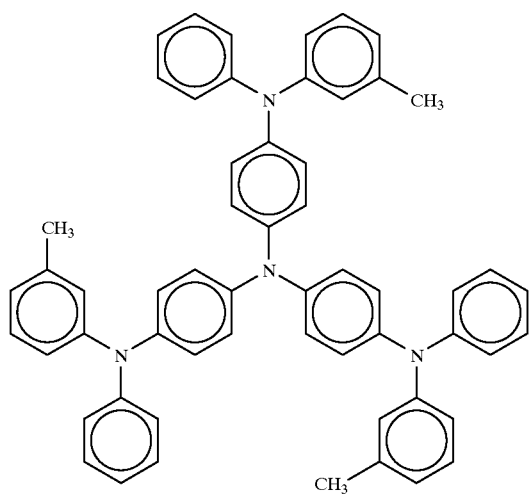 93

48 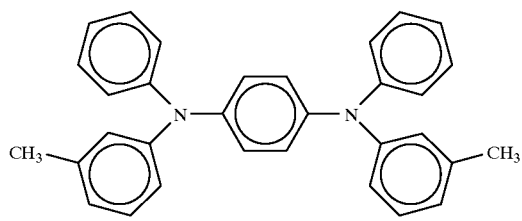 80

What is claimed is:

1. A process for producing a heterocyclic aromatic amine wherein a heterocyclic aromatic halide is reacted with an amine compound in the presence of a base, characterized in that the reaction of the heterocyclic aromatic halide with the amine compound is effected by using a catalyst comprising tri-tert.-butylphosphine phosphine and a palladium compound.

2. A process for producing an arylamine wherein an aryl halide is reacted with an amine compound in the presence of a base, characterized in that the reaction of the aryl halide with the amine compound is effected by using a catalyst comprising tri-tert.-butylphosphine and a palladium compound.

* * * * *